(12) United States Patent
Manoharan

(10) Patent No.: US 6,576,783 B2
(45) Date of Patent: Jun. 10, 2003

(54) OLIGONUCLEOTIDE PROTECTING GROUPS

(75) Inventor: Muthiah Manoharan, Carlsbad, CA (US)

(73) Assignee: ISIS Pharmaceuticals, Inc., Carlsbad, CA (US)

(*) Notice: Subject to any disclaimer, the term of this patent is extended or adjusted under 35 U.S.C. 154(b) by 221 days.

(21) Appl. No.: 09/745,642

(22) Filed: Dec. 22, 2000

(65) Prior Publication Data

US 2001/0053855 A1 Dec. 20, 2001

Related U.S. Application Data

(62) Division of application No. 09/148,763, filed on Sep. 4, 1998, now Pat. No. 6,166,239.

(51) Int. Cl.[7] .................... C07C 69/96; C07C 277/00
(52) U.S. Cl. ............... 558/269; 558/268; 558/260; 560/302; 536/25.3
(58) Field of Search ................... 558/268, 260, 558/269; 560/302; 536/25.3

(56) References Cited

PUBLICATIONS

Barber–Peoch, I. et al., "Solid Phase Conjugation Chemistry: Use of Alloc as a Protecting Group for 2'–Aminolinker Containing Oligonucleotides", *Nucleosides & Nucleotides*, 1997, 16(7–9), 1407–1410.

Ghosh, A.K., "Di(2–Pyridyl) Carbonate Promoted Alkoxycarbonylation of Amines: A Convenient Synthesis of Functionalized Carbamates", *Tetra. Lett.*, 1991, 32(34), 4251–4254.

Hawyakawa, Y. et al., "The Allylic Protection Method in Solid–Phase Oligonucleotide Synthesis. An Efficient Preparation of Solid–Anchored DNA Oligomers", *J. Am. Chem. Soc.*, 1990, 112, 1691–1696.

Kunz, H. et al., "Der Allyloxycarbonyl(Aloc)–Rest–die Verwandlung einer untauglichen in eine wertvolle Aminoschutzgruppe fur die Peptidsynthese," *Angew. Chem. Int. Ed. Engl.*, 1984, 96(6), 426–427 (English abstract included).

Manoharan, M., "Designer Antisense Oligonucleotides: Conjugation Chemistry and Functionality Placement", *Antisense Research and Applications*, 1993, CRC Press, Boca Raton, 303–349.

Nelson, P.S. et al., "3'–Terminal Modification of Oligonucleotides Using a Universal Solid Support", *Nucleosides & Nucleotides*, 1997, 16(10 & 11), 1951–1959.

*Primary Examiner*—James O. Wilson
*Assistant Examiner*—Howard V Owens, Jr.
(74) *Attorney, Agent, or Firm*—Woodcock Washburn LLP

(57) ABSTRACT

Methods of preparing bis-protected guanidino groups of formula (IX)

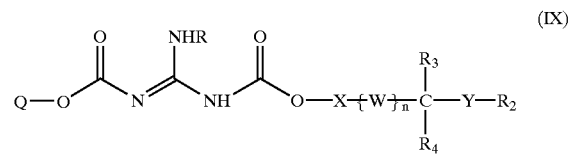

comprising the steps of reacting a compound of formula (VIII)

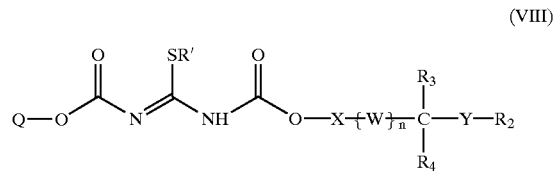

with an amine, wherein R' is a thiopseudourea protecting group. Guanidino (IX) may then be used to add a guanidino functionality to other compounds, in particular those with a reactive hydroxyl group to give a protected functional group —NH—C(NH)—NH—CO—O—$(CR_5R_6)N$—$CR_3R_4$—Y—$R_2$.

2 Claims, No Drawings

OLIGONUCLEOTIDE PROTECTING GROUPS

This patent application is a divisional of U.S. application Ser. No. 09/148,763, filed on Sep. 4, 1998, now U.S. Pat. No. 6,166,239, the disclosure of which is incorporated herein by reference.

FIELD OF THE INVENTION

The present invention relates to protecting groups, more particularly to compounds useful for protecting amino, amidino, guanidino and hydroxyl groups, as well as methods of use thereof during oligonucleotide synthesis.

BACKGROUND OF THE INVENTION

During oligonucleotide synthesis, convenient amino group protection methodology is important not only for exocyclic amines but also for side chain amino groups ("aminolinkers" or "aminotethers"). These amino group-containing tethers can be conveniently deprotected and used to attach various functionalities to modify the biological or chemical properties of oligonucleotides (e.g., to conjugate groups which can improve uptake of antisense oligonucleotides by living cells); to attach chemical nucleases targeting the pathogenic genes; and to attach reporter groups (such as fluorescein or biotin) which are extensively used in DNA based diagnostics in following cellular trafficking of antisense oligonucleotides (Manoharan, M., in Antisense Research and Applications, S. T. Crooke and B. Lebleu (eds.), CRC Press, Boca Raton, Fla., 1993, 303–349). In spite of their widespread use, the conventional protecting groups used in oligonucleotide chemistry for aminotethers are either too labile during the monomer synthesis (e.g., $CF_3CO-$, Fmoc) or somewhat inert, thereby requiring harsh conditions during, for example, oligonucleotide deprotection. The phthalimido group, for example, requires $CH_3NH_2$ in addition to the standard ammonium hydroxide conditions. The acid labile MMT (monomethoxytrityl) group is sometimes used, but generally to protect an aminolinker only at the 5'-end of the oligonucleotide.

To overcome these problems the alloc (allyloxycarbonyl) group (Kunz. H. Angew. Chem. 96, 426, 1984; Hayakawa, Y.; Wakabayashi, S.; Kato, H.; Noyori, R. J. Am. Chem. Soc. 112, 1691, 1990) has been adopted as a protecting group for aminolinkers, as it can be removed using zerovalent palladium (Pd (0)) either in solution phase or in solid phase (Barber-Peoch, I; Manoharan, M.; Cook, P. D. Nucleosides & Nucleotides 16, 1407–1410, 1997; Nelson, P. S.; Muthini, S.; Kent, M. A; Smith T. H.; Nucleosides & Nucleotides 16, 1951–1959, 1997). The chloroformate Cl—(C=O)—O—CH2—CH2—CN also has been used to protect nucleobase amines. Chloroformates, however, are unstable and difficult to use. It would therefore be desirable to provide alternative reagents for protecting amine and other groups during synthesis.

SUMMARY OF THE INVENTION

In one aspect, the present invention provides compounds of the formula (I)

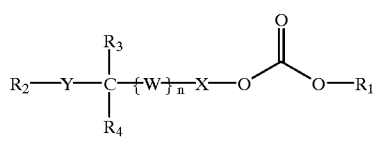

(I)

wherein
X is aryl or a covalent bond;
Y is aryl or a covalent bond;
$R_1$ is selected from succinimid-N-yl, phthalimid-N-yl, pyridin-N-yl, 4-nitrophenyl, N-imidazol-1-yl, benzotriazol-2-yl, pyridin-2-yl, pentafluorophenyl, tetrafluorophenyl, triazol-N-yl, tetrazol-N-yl and norbornan-N-yl;
$R_2$ is cyano, nitro or $CF_3$;
$R_3$ and $R_4$ are each independently selected from the group consisting of H, alkyl, alkenyl, alkynyl, aryl, aralkyl, cycloalkyl and cycloalkyl-alkyl;
W is $C(R_5)(R_6)$ or $C(R_7)=C(R_7)$ where each $R_5$, $R_6$, and $R_7$ is independently selected from the group consisting of H, alkyl, alkenyl, alkynyl, aryl, aralkyl, cycloalkyl and cycloalkyl-alkyl or both $R_7$ substituents together form an unsaturated aromatic ring; and
n is an integer from 0 to 7.

In another aspect, the invention provide methods for protecting amine, guanidine, amidine or hydroxyl groups comprising reacting a free amine, guanidine, amidine or phosphate with a compound according to the general formula (I).

DETAILED DESCRIPTION OF THE INVENTION $R_1$ can be selected from succinimid-N-yl, phthalimid-N-yl, pyridin-N-yl, 4-nitrophenyl, -imidazol-1-yl, benzotriazol-2-yl, pyridin-2-yl, pentafluorophenyl, tetrafluorophenyl, triazol-N-yl, tetrazol-N-yl, pyrazol-N-yl and norbornan-N-yl. More preferably, $R_1$ is succinimid-N-yl, phthalimid-N-yl or pyridin-N-yl, and even more preferably succinimid-N-yl or phthalimid-N-yl. Most preferably, $R_1$ is succinimid-N-yl.

$R_2$ can be cyano, nitro or $CF_3$. In a preferred embodiment, $R_2$ is cyano while X and Y are both a covalent bond. In another preferred embodiment $R_2$ is nitro while one of X and Y is aryl while the other is a covalent bond. In another embodiment R2 is cyano while Y is aryl (e.g., 1,4-phenylene) and X is a covalent bond.

$R_3$, $R_4$, $R_5$, $R_6$, and $R_7$ each be independently selected from the group consisting of H, alkyl, alkenyl, alkynyl, aryl, aralkyl, cycloalkyl and cycloalkyl-alkyl.

As used herein, the term "alkyl" includes but is not limited to straight chain, branch chain, and cyclic unsaturated hydrocarbon groups having 1 to about 10 (preferably 1 to about 4) carbon atoms. "Alkenyl" includes but is not limited to straight chain, branch chain, and cyclic saturated hydrocarbon groups having 2 to about 10 carbon atoms. "Alkynyl" includes but is not limited to hydrocarbon groups having 2 to about 10 carbon atoms and a carbon—carbon triple bond. By "cycloalkyl" is meant mono- or bicyclic rings of 3 to 10 members optionally unsaturated and optionaly attached to the carbon atom from which $R_3$ to $R_7$ depend by an alkyl chain thereby forming a "cycloalkyl" group. When any of $R_3$ through $R_7$ is alkenyl or alkynyl, the unsaturated bond or bonds preferably are spatially removed from the carbon atom from they depend. In other words, the unsaturated bond is preferably not adjacent to said carbon atom.

"Aryl" is used herein interchangeably with "aromatic", and includes optionally substituted mono-, bi- and tricyclic, 5 to 14 membered rings incorporating carbon atoms exclusively or incorporating one or more heteroatoms such as N, O and S (as well as SO and $SO_2$), thereby forming a heteroaryl group. Prefered aryl groups include phenyl, naphthyl, pyridyl, quinolinyl, isoquinolinyl and naphthyridyl.

In preferred embodiments, $R_3$ through $R_7$ are independently H, alkyl or aryl. In a particularly prefered embodiment $R_3$, $R_4$ and $R_5$ are H and $R_6$ is phenyl (preferably while n is 1). In another particularly prefered embodiment, both $R_3$ and $R_4$ are H and both $R_5$ and $R_6$ are methyl (preferably while n is 1). In another preferred embodiment, each of $R_3$ through $R_6$ are H (preferably while n is 1).

In other embodiments in which W includes olefinic moieties, $R_2$ preferably is cyano or nitro. When W is olefinic, adjacent $R_7$ substituents together may form an aromatic ring. Prefered aromatic (i.e., aryl) rings formed in this respect include benzene, naphthalene, pyridine and more preferably benzene.

X and Y preferably are both covalent bonds. In an alternate embodiment, one of X and Y is aryl (e.g., 1,4-phenylene) wherein X and $CR_5R_6$ are para to one another.

Compounds of the invention can be prepared according established organic synthetic techniques. In a particular general method, compounds are prepared by reacting an alcohol of formula (II) under suitable conditions (e.g. in acetonitrile/dichloromethane in the presence of pyridine) with a dicarbonate of formula (III), wherein X, Y, n and $R_1$ through $R_7$ are as previously defined. See Scheme 1 below. The alcohol (II) and dicarbonate (III) are either commercially available or themselves are prepared from commercially available reagents according to established synthetic techniques.

Scheme 1

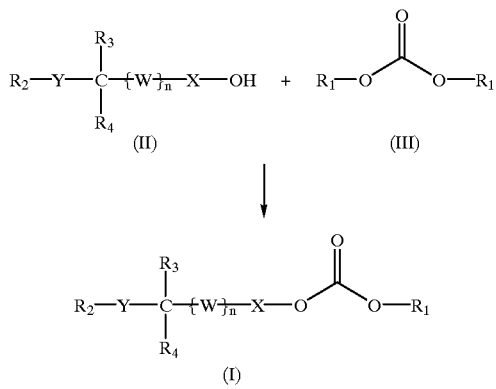

Alternatively, compounds of formula (I) can be prepared by reacting a chloroformate of formula (IV) under suitable conditions with an alcohol of formula (V). See Scheme 2 below.

Scheme 2

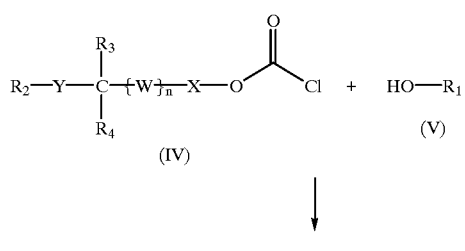

-continued

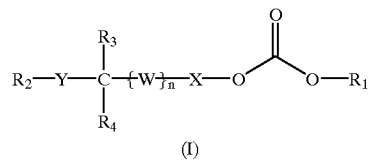

Again, chloroformate (IV) and alcohol (V) are either commercially available or themselves may be prepared from commercially available reagents using established organic synthetic techniques.

The invention also provides methods for protecting amine, guanidine, amidine or hydroxyl groups comprising reacting a free reactive amine, guanidine, amidine, or hydroxyl with a compound according to the general formula (I). Said amine, guanidine, amidine or hydroxyl group may be incorporated on or within various chemical molecular entities requiring protection, including but not limited to amino acids, peptides, proteins, nucleosides (RNA or DNA), nucleotides and oligonucleotides. In particular, amino acids incorporating amines and guanidines in their side chains (e.g., lysine and arginine, respectively) are suitable for methods of the invention. Other compounds particularly amenable to the present invention are nucleosides, nucleotides and oligonucleotides. For instance, exocyclic amine groups on nucleobases (e.g., cytosine, adenine and guanine) can be protected according to methods of the invention. A class of nucleosides known as "peptide nucleic acids" (PNAs) incorporate a peptidic backbone in place of a natural sugar-phosphate backbone, the amine group of which may also be protected according the method of the invention. Further, hydroxyl groups on the sugar of a nucleoside (e.g., at the 2'-, 3'- and 5'-positions) also can be protected.

In a particular embodiment, the amine, amidine, guanidine and hydroxyl groups that are protected according to the present invention are located on tethering or linker groups. The amine, amidine, guanidine or hydroxyl groups on these tethers can, upon deprotection, be used to attach functional groups to nucleosides, nucleotides, and, in particular, oligonucleotides to modify the biological or chemical properties of such moieties. Functional groups include conjugate groups (such as cholesterol) for enhancing cellular uptake, intercolators for enhancing hybridization, chemical nucleases for targeting pathogenic genes, and reporter groups (such as fluorescein and biotin) for diagnostic purposes or monitoring cellular trafficking. Tethers can be attached to the nucleobase, backbone or sugar moieties. In a particular embodiment, tethers are attached at the 2'-O position of a nucleoside sugar. Alternatively, tethers may be attached at the 3'-O position, for example when oligonucleotides have one or more 2'–5' linkage or at the 5'-O position when the tether is at the 5' terminus of an oligonucleotide.

Protecting groups may be subsequently removed to give the free amine, amidine, quanidine or hydroxy by reacting with a suitable reagent. For amines, amidines and guanidines, suitable removing agents include ammonium hydroxide ($NH_4OH$), triethylamine ($NEt_3$), DBU, Hunig's base, (iPr)2NEt, Et2N4, piperidine, morpholine, piperazine and pyrrolidine. For hydroxyl groups, suitable reagents for removing protecting groups include DBU. Advantageously, one can achieve deprotection of all amine groups (nucleobase and tethered amines) and all phosphates of an oligonucleotide synthesis in a single step. This is accomplished when a suitable phosphate protecting group is employed such as β-cyanoethyl and a suitable deprotection reagent is used such as ammonium hydroxide. Alternatively, the protecting group may be employed at specified groups and not at others, thereby affording selective protection/deprotection ability.

In one aspect of the invention, compounds of formula (I) are used in a guanylating process. A thiopseudourea of formula (VI) (wherein R' is a suitable protecting group such as alkyl, e.g. methyl) is reacted with a dicarbonate of formula (III) to give a mixture of mono and bis protected thiopseudourea (VII) and (VIII) (wherein Q is —X—$(CR_5R_6)_n$—$CR_3R_4$—Y—$R_2$). The bis compound (VIII) is then reacted with a primary amine $RNH_2$ wherein R is H or a guanidino protecting group such as alkyl (e.g., methyl) or BOC to give a bis protected guanidino group (IX). Guanidino (IX) may then be used to add a guanidino functionality to other compounds, in particular those with a reactive hydroxyl group to give a protected functional group —NH—C(NH)—NH—CO—O—$(CR_5R_6)$N—$CR_3R_4$—Y—$R_2$. Deprotection of the guanidinyl group may achieved using a suitable reagent including base.

Scheme 3

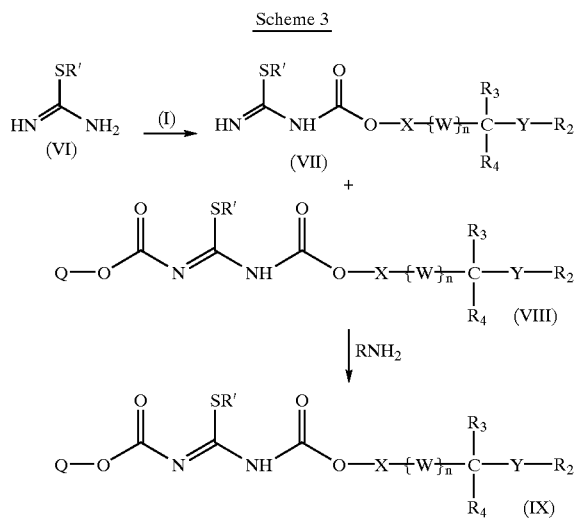

Additional objects, advantages, and novel features of this invention will become apparent to those skilled in the art upon examination of the following examples thereof, which are not intended to be limiting.

EXAMPLE 1

Preparation of Cyanoethyloxycarbonyloxy Succinimide (Compound 1)

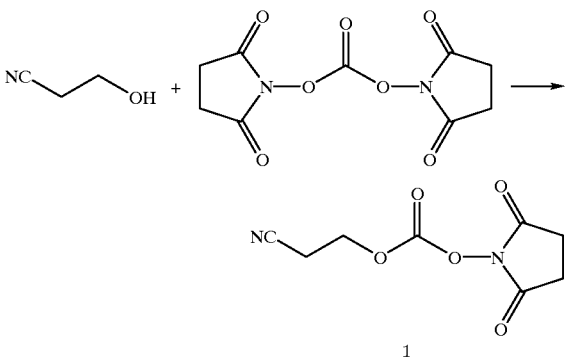

To 3.0 g of 2-cyanoethanol (42.21 mmol) in 140 mL anhydrous $CH_3CN$, 17 g of N,N'-disuccinimidyl carbonate (Fluka, 66 mmol) was added followed by 5.5 mL of pyridine. The suspension became a clear solution after about 1 hr. The solution was shaken for an additional 1 hr, and then evaporated. The solution was redissolved in 100 mL of $CH_2Cl_2$, washed with 5% $NaHCO_3$ solution followed by saturated NaCl solution. The organic layer was dried over anhydrous $MgSO_4$ and evaporated to give 8.5 g of a creamy white solid (95% crude yield). The crude product was purified in silica gel using $CH_2Cl_2$:EtOAc (50:50) to give 7.2 g of a white crystalline compound 1. (Rf=0.21) $^1$H NMR ($CDCl_3$) (2.85, s, 4H; 2.75 t, —$CH_2$—CN; 4.45, t, —$CH_2$—O—) M.P. 104.1° C.

$^{13}$C NMR (DMSO); 169.82 (N—$\underline{C}$≡O) 150.91 (—O—$\underline{C}$(=O)—O) 117.91 (C≡N) 65.86 (—$CH_2$—O—) 25.39 (—CH—C—) 17.33 (—$CH_2$CN).

EXAMPLE 2

Preparation of 2'-O-aminoethyl-5'-O-DMT-5-methyluridine (Compound 4)

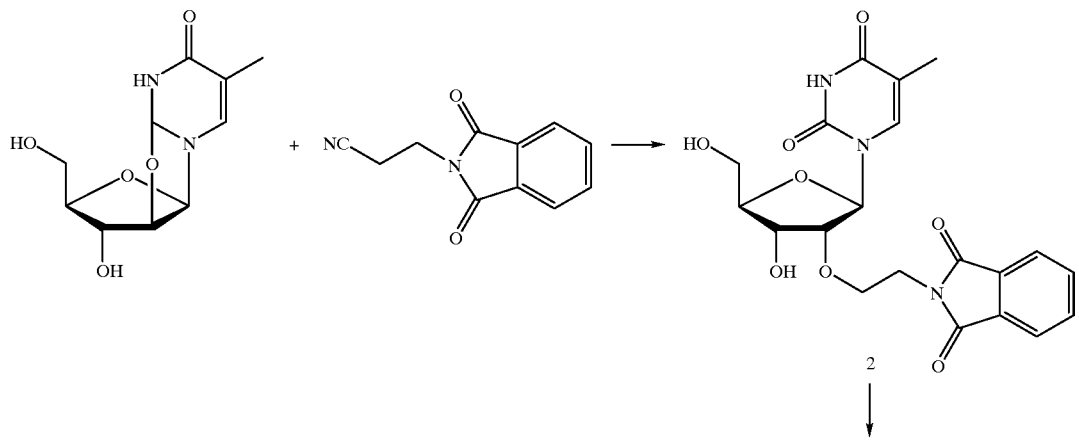

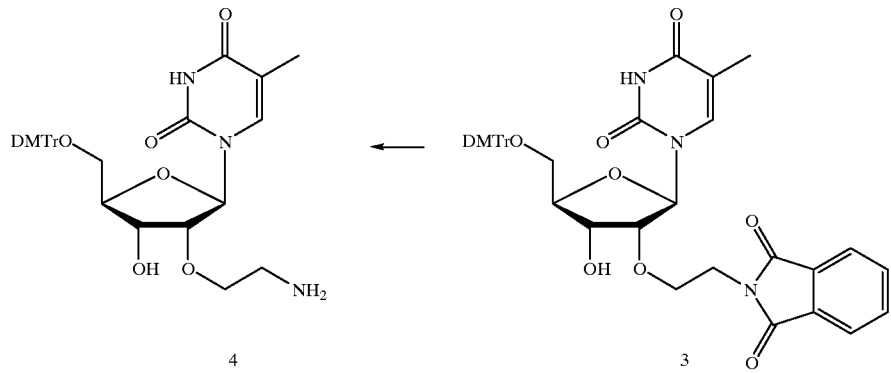

N-(2-hydroxyethyl)phthalimide (277 g, 1.45 mol) was slowly added to a solution of borane in tetrahydrofuran (1M, 600 mL) with stirring. Hydrogen gas evolved as the solid dissolved. Once the rate of bubbling subsided, the solution was placed in a 2L stainless steel bomb. 2,2'-anhydro-5-methyluridine (60 g, 0.25 mol) and sodium bicarbonate (120 mg) were added and the bomb was sealed. After 30 minutes, the bomb was vented for the last time and then placed in an oil bath and heated to 150° C. internal temperature for 24 h. The bomb was then cooled to room temperature and opened. TLC revealed all the starting material was gone. The crude solution was concentrated and the residue was colummned on silica gel starting with straight ethyl acetate to remove excess phthalimide reagent followed by ethyl acetate-methanol 95/5 to elute the product to give 22.2 g (20.6%) of ca 90% pure product 2.

2'-O-phthalimidoethyl-5-methyluridine 2 (22.2 g, 0.053 mol) was coevaporated with pyridine (2×75 mL) and then dissolved in 100 mL of pyridine. Dimethoxytrityl chloride (27 g, 0.080 mol) was added in one portion with stirring. TLC after 1 h indicated a complete reaction. Methanol (10 mL) was added to quench the reaction. The reaction was concentrated and the residue partitioned between ethyl acetate and saturated sodium bicarbonate solution (150 mL each). The organic layer was concentrated and the residue was dissolved in a minimum amount of dichloromethane and applied on a silica gel column. The compound was eluted with ethyl acetate-hexanes-triethylamine (50:50:1 to 80:20:1) to give 26.1 g (82%) of pure product 2'-O-phthalimidoethyl-5'-O-DMT-5-methyluridine 3.

2'-O-phthalimidoethyl-5'-O-DMT-5-methyluridine 3 (21.1 g, 0.29 mol) was dissolved in methanol (500 mL). Anhydrous hydrazine (4.9 mL, 0.15 mol) was added and the solution was heated to reflux. TLC after 3 h indicated a complete reaction. The solution was concentrated and columned on silica gel using methanol and then methanol-ammonium hydroxide (98:2) to give 10.4 g of pure product 2'-O-aminoethyl-5'-O-DMT-5-methyluridine 4 as a white foam and 2 g of slightly contaminated product (total yield 12.4 g, 71%).

EXAMPLE 3

Preparation of 2'-O-[N-cyanoethyloxy-carbonyl-2-(aminoethyl)]-5'-O-dimethoxy-trityl-5-methyluridine (Compound 5)

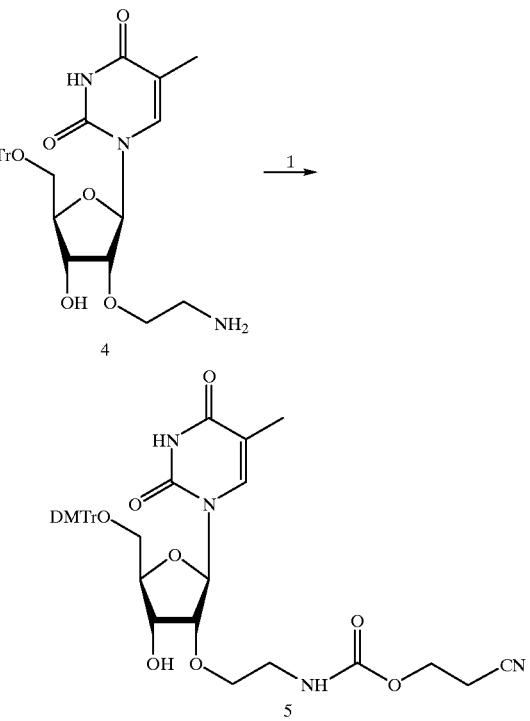

To cyanoethyloxycarbonyloxy-N-succinimide 1 in 10 mL of $CH_2Cl_2$ was added 0.5 mL of pyridine followed by 1.43 g of 2'-O-(aminoethyl)-5'-O-DMT-5-methyluridine (compound 4, 2.35 mmol) and stirred for 1 hr. TLC ($CH_2Cl_2$/$CH_3OH$ 9:1; Rf=0.48) indicated complete conversion of amine to the carbamate derivative. The mixture was then diluted with $CH_2Cl_2$ (50 mL) and washed successively with aqueous $NaHCO_3$ solution, saturated NaCl solution and dried over $MgSO_4$. Chromatography over silica and elution with $CH_2Cl_2$:EtoAc gave the product 5 (1.2 g, 73%).

EXAMPLE 4
Preparation of 2'-O-[N-cyanoethyloxy-carbonyl-2-(aminoethyl)]-3'-O-[N,N-diisopropyl-aminocyanoethyloxyphosphoramidite]-5'-O-DMT-5-methyluridine (Compound 6)

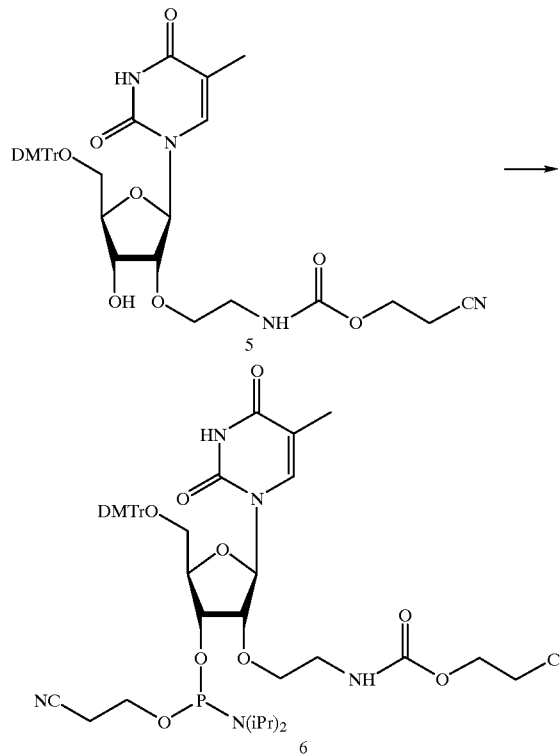

5'-O-DMT-2'-O-(N-cyanoethyloxy carbonyl aminoethyl)-5-methyl-uridine 5 (700 mg, 1 mmol) was dissolved in 15 mL of dry $CH_2Cl_2$ and to this solution 85 mg of diisopropylaminotetrazolium salt (0.5 mmol) followed by 420 μL of 2-cyanoethyl-N,N,N'N'-tetraisopropyl phosphoramidite was added slowly using a syringe under argon. The mixture was stirred at room temperature over night and in the morning the TLC indicated almost complete. 40 μL of the phosphitylation reagent was added and stirred for an additional 2 hrs. TLC then indicated complete conversion of the starting material to the phosphoramidite ($CH_2Cl_2$:EtOAc 50:50; Rf=0.33). The reaction mixture was diluted with 50 mL $CH_2Cl_2$, washed with saturated $NaHCO_3$ solution followed by saturated NaCl solution. The organic layer was dried over $MgSO_4$ and evaporated to dryness. The crude foam was purified in silica gel and eluted with 50:50 ethylacetate:$CH_2Cl_2$ to give compound 6. Yield=720 mg (81%) $^{31}P$ NMR: $CDCl_3$ (149.5 ppm and 150.5 ppm)

EXAMPLE 5
Solid Phase Synthesis of Oligonucleotides Incorporating CEOC Protected 2'-O-aminoethyl Nucleosides 2'-O-[N-cyanoethyloxycarbonyl-2-(aminoethyl)]-3'-O-[N,N-diisopropyl-aminocyano-ethyloxy phosphoramidite] 5'-O-DMT-5-methyl uridine (compound 6, 192 mg, 0.2 mmol) was dissolved in 2 mL of anhydrous acetonitrile and loaded onto an Expedite Nucleic Acid Synthesis system (Millipore) to synthesize oligonucleotides incorporating CEOC-amino protected nucleosides. The amidite concentration was 0.1M. The coupling efficiencies were more than 90%. When coupling the first amidite, the coupling time was extended to 10 min. and the step carried out twice. All other steps in the protocol supplied by Millipore were used. Oligonucleotides were cleaved from the controlled pore glass (CPG) support and deprotected (including CEOC groups) under standard conditions using concentrated aqueous $NH_4OH$ (30%) at 55° C. 5'-O-DMT-containing oligonucleotides were then purified by reverse phase high performance liquid chromatography (C-4, Waters, 7.8×300 mm, A-100 mm triethylammonium acetate, pH 7; B=acetonitrile; 8–18% of B in 30 minutes; flow 1.5 mL/min.). Detritylation with aqueous 80% acetic acid and evaporation, followed by desalting in a Sephadex G-25 column gave oligonucleotides incorporating 2'-O-aminoethyl nucleotides which were analyzed by CGE and mass spectrometry (see Table 1).

EXAMPLE 6

Preparation of 2'-O-[N-cyanoethyloxy-carbonyl-(6-aminohexyl)]-5'-O-dimethoxy-trityl-5-methyl-uridine (Compound 7)

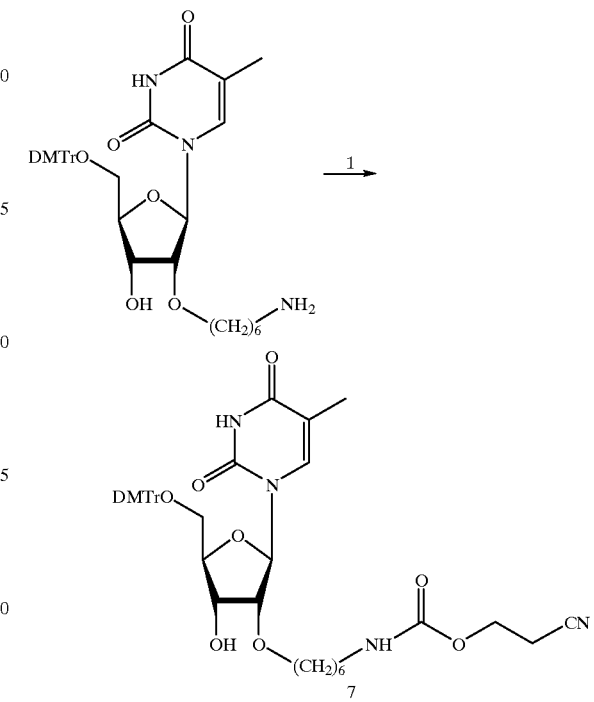

To 3.3 g of 2'-O-(6-aminohexyl)-5'-O-dimethoxytrityl-5-methyl uridine (prepared according to the same procedure as for compound 4) (5 mmol) in 20 mL of anhydrous $CH_2Cl_2$, 1 mL of pyridine was added followed by 1.2 g (5.6 mmol) of 2-cyanoethyloxycarbonyloxy succinimide. The reaction mixture was stirred for 2 hrs and tested for completion of reaction by TLC ($CH_2Cl_2$:$CH_3OH$ 9:1). Reaction mixture was applied to silica gel equilibrated with $CH_2Cl_2$:$CH_3OH$ 9:1 and eluted with the same (Rf=0.51). Yield=3.13 g, 82%. $^1H$ and $^{13}C$ NMR affirmed the expected compound 7.

EXAMPLE 7
Preparation of 5'-O-DMT-2'-O-[N-cyanoethyloxy-carbonyl-(6-aminohexyl)]-5-methyl uridine-3'-O-(N,N-diisopropylamino-2-cyanoethyloxy)phosphoramidite (Compound 8)

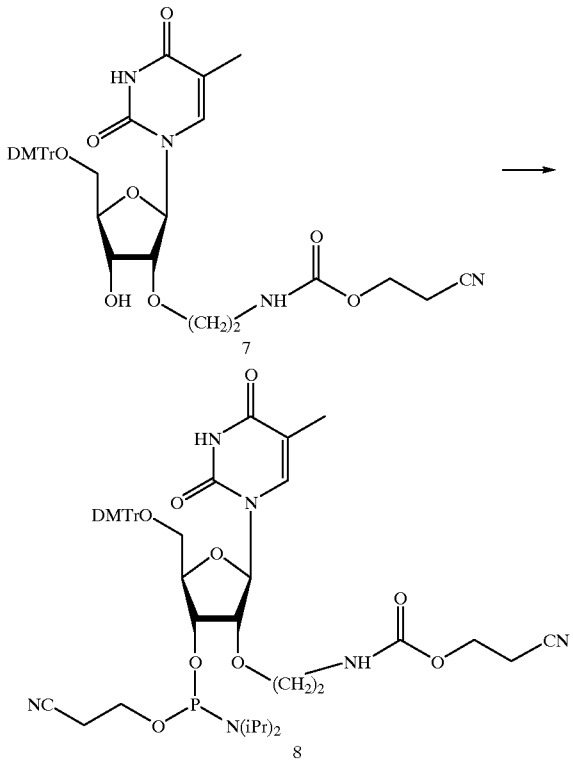

2'-O-[N-cyanoethyloxycarbonyl-(6-aminohexyl)]-5'-O-dimethoxytrityl-5-methyl-uridine 7 (1.51 g, 2 mmol) was dissolved in 30 mL of anhydrous $CH_2Cl_2$ and to this solution 170 mg of diisopropylamino tetrazolium salt (1 mmole) followed by N,N,N'N'-tetraisopropyl phosphoramidite (990 µL, 2.6 mmols) under argon atmosphere. The reaction mixture was stirred for 16 hrs. TLC analysis (50:50 $CH_2Cl_2$/ ethylacetate) indicated completion of the reaction. The reaction mixture was then diluted with 100 mL of $CH_2Cl_2$, extracted with saturated $NaHCO_3$ solution, washed with saturated NaCl solution and dried over $MgSO_4$. Evaporation to dryness gave a white foam which was applied on the top of silica gel made with $CH_2Cl_2$ containing 0.1% pyridine. The amidite was loaded in $CH_2Cl_2$ and eluted with 40:60 $CH_3COOEt/CH_2Cl_2$ to give 1.3 g of purified amidite 8 (68% yield). $^{31}P$ NMR=150.5, 151 ppm.

EXAMPLE 8
Solid Phase Synthesis of Oligonucleotides Incorporating CEOC Protected 2'-O-aminohexyl Nucleosides 5'-O-DMT-2'-O-[N-cyanoethyloxy-carbonyl-(6-aminohexyl)]-5-methyl uridine-3'-O-(N,N-diisopropylamino-2-cyanoethyloxy) phosphoramidite (compound 8) (400 mg, 0.39 mmol) was dissolved in 3.9 mL of anhydrous acetonitrile and loaded onto an Expedite Nucleic Acid Synthesis system (8909) (Millipore) to synthesize the oligonucleotides. The amidite concentration was 0.1M. The coupling efficiencies were more than 90%. When coupling the first amidite, the coupling time was extended to 10 min. and this step was carried out twice. All other steps in the protocol supplied by Millipore were used. Oligonucleotides oligomers were cleaved from the controlled pore glass (CPG) supports and deprotected (including cyanoethyloxy-carbonyl protecting groups) under standard conditions using concentrated aqueous $NH_4OH$ (30%) at 55° C. 5'-O-DMT-containing oligomers were then purified by reverse phase high performance liquid chromatography (C-4, Waters, 7.8× 300 mm, A=50 mM triethylammonium acetate, pH −7, B=acetonitrile, 5–60% of B in 60 min., flow 1.5 mL/min.). Detritylation with aqueous 80% acetic acid and evaporation, followed by desalting in a Sephadex G-25 column gave oligonucleotides incorporating 2'-O-aminohexyl nucleotides (see Table 1) which were analyzed by HPLC, CGE and mass spectrometry.

EXAMPLE 9
6-(N-2-cyanoethyloxycarbonyl)aminohexanol (Compound 9)

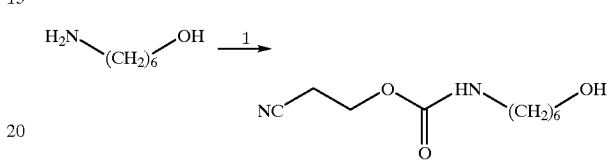

6-Aminohexanol (0.5 g, 4.23 mmol) was dissolved in anhydrous $CH_2Cl_2$ (10 mL). Compound 1 (1.08 g, 5.09 mmol) was added and stirred for 2 hrs. The reaction was followed by TLC (5% MeOH in CH2Cl2). Solvent was removed under vacuum and residue was placed on a flash column and eluted with 5% MeOH in $CH_2Cl_2$ to get 9 as a white powder (0.883 g, 96% yield). Rf (0.28, 5% MeOH in $CH_2Cl_2$). $^1H$ NMR ($CDCl_3$) δ 4.9 (br, 1H), 4.3 (t, 2H, J=6.12 Hz), 3.68 (3H, t, J=3.71 Hz), 2.73 (2H, t, J=6.12 Hz), 1.6–1.39 (m, 8H). $^{13}C$ NMR ($CDCl_3$) d 155.64 (C=O), 117.34 (C≡N), 62.49, 59.01, 40.92, 32.47, 29.73, 26.35, 25.30, 18.49. MS ($APCI^+$) calculated for $C_{10}H_{19}O_3N_2^+$ 215; observed 215.1.

EXAMPLE 10
6-(N-2-cyanoethyloxycarbonyl)aminohexyl-β-cyanoethyl-N,N-diisopropyl Phosphoramidite 10

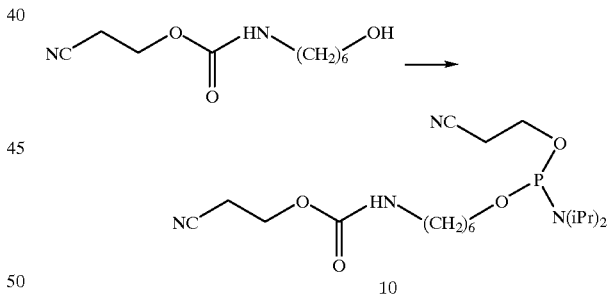

Compound 9 (0.72 g, 3.36 mmol) was mixed with diisopropylamine tetrazolide (0.29 g, 1.68 mmol). The mixture was then dried over $P_2O_5$ under high vacuum overnight at 40° C. The reaction mixture was flushed with argon. Anhydrous acetonitrile (16.95 mL) was added, followed by dropwise addition of 2-cyanoethyl-N,N,N',N'-tetraisopropyl phosphorodiamidite (1.52 g, 5.04 mmol). The reaction mixture was stirred at room temperature for 4 hrs under argon atmosphere. Solvent was removed under vacuum. The residue was placed on a flash column and eluted with ethylacetate:hexane 1:1 to get compound 10 as an oil (44% yield). Rf (0.05, ethylacetate:hexane, 1:1) $^1H$ NMR ($CDCl_3$) δ 4.29 (t, 2H, J=6.24 Hz), 3.53–3.95 (m, 6H), 3.21 (Q, 2H, J=6.46, 6.78), 2.62–2.75 (m, 4H), 1.48–1.7 (M, 8H), 1.22 (S, 6H), 1.22 (S, 6H). $^{31}P$ NMR ($CDCl_3$) δ 147.78, MS ($FAB^+$) calculated for $C_{19}O_4H_{35}NAPNa^+$=437; observed 437.

EXAMPLE 11
Solid Phase Synthesis of Oligonucleotides Incorporating CEOC Protected Aminohexanol Amidite 10 (0.060 g, 0.14 mmol) was dissolved in anhydrous acetonitrile (1.4 mL) and loaded onto an Expedite Nucleic Acid Synthesis System (Millipore) to synthesize the oligonucleotide. Commercially available dA, dC, T and dG amidites were used to synthesize oligonucleotide. Coupling efficiencies were more than 95%. All other steps in the protocol for 1 mmol DNA synthesis supplied by Millipore were used except the extended coupling time (10 min.) for amidite 10. The oligomers were cleaved from the controlled pore glass (CPG) supports and deprotected under standard conditions using concentrated aqueous NH$_4$OH (30%) at 55° C. Fully deprotected oligonucleotide was then purified by HPLC on reverse phase column (C-4, Waters, 7.8×300 mm, A-50 mm triethylammonium acetate, pH 7; B=acetonitrile, 5–60% B in 60 mins., flow 2.5 mL/min.). Purity and integrity of oligonucleotide (oligonucleotide 7 in table I) was established by CGE, HPLC and mass spectrometry. Electrospray mass calculated for M$^+$=6161.68; observed M$^+$=6160.72.

EXAMPLE 12
Conjugation to Fluorescein

Oligonucleotides 4 and 7 (see table 1 below) containing the tethered amino functionality were used to conjugate fluorescein to the oligonucleotide. Purified oligonucleotides (15OD) were taken in 1M NaHCO$_3$/Na$_2$CO$_3$ buffer (100 µL, pH9.2). A solution of fluorescein isothiocyanate (100 µL, 1M solution in DMF) was added to the solution of oligonucleotides and kept at room temperature for 24 hrs. Unreacted fluorescein isothiocyanate was removed by passing the reaction mixture through a Sephadex G-25 and eluting the column with water. Conjugated oligonucleotides were then purified by reverse phase high performance liquid chromatography and characterized by mass spectrometry and analytical HPLC.

EXAMPLE 13
Guanidium Protection

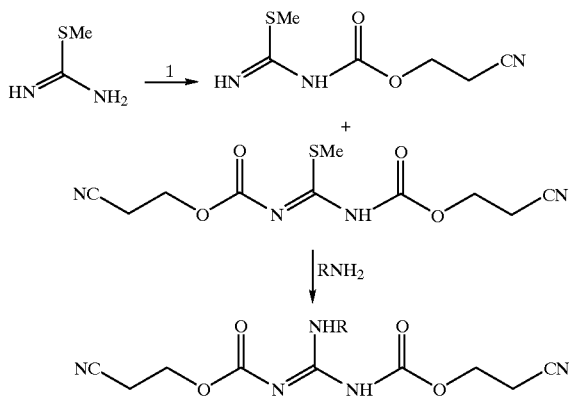

2-Methyl-2-thiopseudourea.1/2H$_2$SO$_4$ (280 mg, 2 mmols) was suspended in 15 mL of CH$_2$Cl$_2$ and 15 mL of 10% NaHCO$_3$. Cyanoethyloxycarbonyloxy succinimide 1 (900 mg, 4.2 mmols) was added and after stirring overnight at room temperature for 2 hrs. The organic layer was separated. The water layer was extracted (3×50 ml) with CH$_2$Cl$_2$ and the combined organic layers were dried over MgSO$_4$. TLC indicated two products. The dried organic solution was evaporated and eluted with 5% ethyl acetate in methylene chloride followed by 10% ethyl acetate in methylene chloride. The fast moving compound was the desired bis CEOC compound (N,N'-bis-CEOC-2-methyl-2-thiopseudourea) and the slow moving compound is the mono CEOC compound. Yield of 6=520 mg.

Primary amine was dissolved in DMF (1 mmol in 3 mL). Triethylamine (1 eq.) and N,N'-bis CEOC-2-methyl-2-thiopseudourea (1.1 equivalent) were added. After stirring for 3 hrs at room temp, TLC indicated completion of reaction and water was added. The mixture was extracted with ethyl acetate and purified by silica gel column chromatography.

EXAMPLE 14
Preparation of Cyanoethyloxycarbonyloxy Pyridine-2-yl

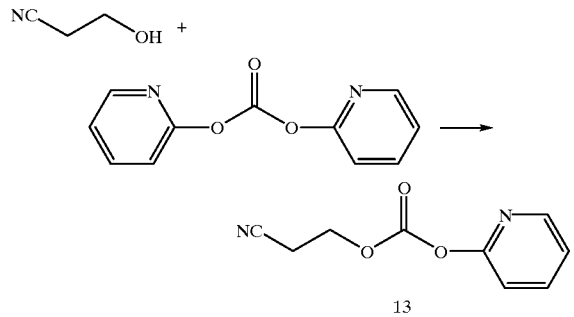

To a solution of β-cyanoethanol (0.3 g, 4.22 mmol) in CH$_2$Cl$_2$ (31.7 mL), 13, di(2-pyridyl)carbonate (1.37 g, 6.34 mmol) was added (Ghosh, A. K.; Duong, T. McKee, S. P. Tetrahedron Lett. 32, 4251, 1991). Triethylamine (0.8 mL, 6.34 mmol) was added to the above solution and the reaction mixture was stirred at ambient temperature for 8 hrs. TLC showed disappearance of starting material. Solvent was removed under vacuum to give residue 11.

TABLE 1

| Oligo no. | Oligo sequence | 2'-O mod. | Mass exp. | Mass obs. | HPLC ret. time[c] |
|---|---|---|---|---|---|
| 1 | GAT*CT[d] | aminohexyl | 1895.00 | 1895.57[a] | 20.05 |
| 2 | T*CCAGGT*GT*CCGCAT*C | aminohexyl | 5599.00 | 5597.24[a] | 24.01 |
| 3 | CTCGTACT*T*T*T*CCGGTCC | aminohexyl | 5853.21 | 5854.56[b] | 20.25 |
| 4 | CTAGTACCT*TTCCGGTCC | aminohexyl | 5493.21 | 5493.91[b] | 16.47 |
| 5 | GAT*CT | aminoethyl | 1837.00 | 1837.00[a] | 19.92 |
| 6 | T*CCAGGT*GT*CCGGCAT*C | aminoethyl | 5368.00 | 5370.40 | 23.88 |
| 7 | LTGCATCCCCCAGGCCACCAT[f] | — | 6161.68 | 6160.72 | 17.46[e] |
| 8 | CTCGTACCT*TTCCGGTCC | aminohexyl-CS—NH—fluoroscein | 5881.60 | 5880.89 | 22.08[e] |
| 9 | L$_{FL}$TGCATCCCCCAGGCCACCAT[g] | — | 6550.68 | 6550.01 | 23.74[e] |

*2-O modified
[a]DMT-on
[b]DMT-off
[c]minutes; HPLC conditions: C-18 reverse phase column, Waters 3.9 × 300 mm; solvent A = 100 mM triethylammonium acetate pH = 7; solvent B = CH$_3$CN; gradient = 8–18% of B in 30 min.; flow rate = 1.5 mL/min.
[d31]P NMR (in D$_2$O, ppm) −0.05 (single), −0.38 (two), −0.46 (single)
[e]Waters 3.9 × 300 mm; solvent A = 50 mM triethylammonium acetate pH = 7; solvent B = CH$_3$CN, 5–60% B in 55 min.; flow rate = 1.5 mL/min.
[f]L = NH$_2$—(CH$_2$)$_6$—O—
[g]L$_{FL}$ = fluoroscein-NH—CS—NH—(CH$_2$)$_6$—O Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

We claim:

1. A method of preparing a compound of formula (IX)

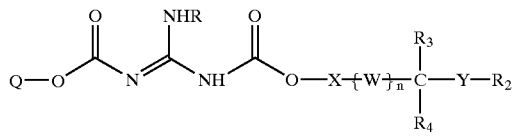

(IX)

wherein
- R is H, or a guanidino protecting group;
- Q is —X—(CR$_5$R$_6$)$_n$—CR$_3$R$_4$—Y—R$_2$;
- X is aryl or a covalent bond;
- Y is aryl or a covalent bond;
- R$_2$ is cyano, nitro or CF$_3$;
- R$_3$ and R$_4$ are each independently selected from the group consisting of H, alkyl, alkenyl, alkynyl, aryl, aralkyl, cycloalkyl and cycloalkyl-alkyl;
- W is C(R$_5$)(R$_6$) or C(R$_7$)=C(R$_7$) where each R$_5$, R$_6$, and R$_7$ is independently selected from the group consisting of H, alkyl, alkenyl, alkynyl, aryl, aralkyl, cycloalkyl and cycloalkyl-alkyl or both R$_7$ substituents together form an unsaturated aromatic ring; and
- n is an integer from 0 to 7;

comprising the steps of:
reacting a compound of formula (VIII)

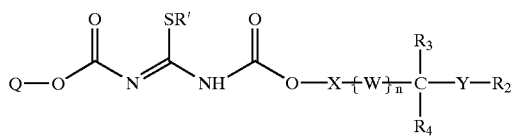

(VIII)

with an amine, wherein R' is a thiopseudourea protecting group.

2. A compound of formula (IX) or formula (VIII):

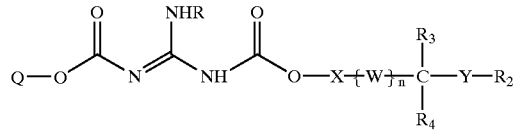

(IX)

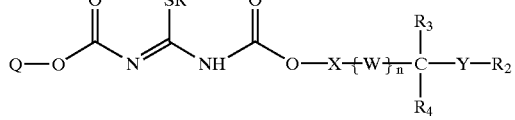

(VIII)

wherein

R is H, or a guanidino protecting group;

Q is —X—(CR$_5$R$_6$)$_n$—CR$_3$R$_4$—Y—R$_2$;

X is aryl or a covalent bond;

Y is aryl or a covalent bond;

R$_2$ is cyano, nitro or CF$_3$;

R$_3$ and R$_4$ are each independently selected from the group consisting of H, alkyl, alkenyl, alkynyl, aryl, aralkyl, cycloalkyl and cycloalkyl-alkyl;

W is C(R$_5$)(R$_6$) or C(R$_7$)=C(R$_7$) where each R$_5$, R$_6$, and R$_7$ is independently selected from the group consisting of H, alkyl, alkenyl, alkynyl, aryl, aralkyl, cycloalkyl and cycloalkyl-alkyl or both R$_7$ substituents together form an unsaturated aromatic ring;

n is an integer from 0 to 7; and

R' is a thiopseudourea protecting group.

* * * * *

UNITED STATES PATENT AND TRADEMARK OFFICE
CERTIFICATE OF CORRECTION

PATENT NO. : 6,576,783 B2
DATED : June 10, 2003
INVENTOR(S) : Muthiah Manoharan

It is certified that error appears in the above-identified patent and that said Letters Patent is hereby corrected as shown below:

<u>Title page,</u>
Item [62], Related U.S. Application Data, please delete "Division of Application No. 09/148,763, file on Sep. 4, 1998, now Pat. No. 6,166,239." and insert therefor
-- The Patent Application is a divisional of U.S. Application Serial No. 09/148,763, field on September 4,. 1998, now U.S. Patent No. 6,166,239, the disclosure of which is incorporated herein by reference. --

Signed and Sealed this

First Day of June, 2004

JON W. DUDAS
*Acting Director of the United States Patent and Trademark Office*